US012133911B2

(12) United States Patent
Morgen et al.

(10) Patent No.: US 12,133,911 B2
(45) Date of Patent: Nov. 5, 2024

(54) FORMULATIONS TO ACHIEVE RAPID DISSOLUTION OF DRUG FROM SPRAY-DRIED DISPERSIONS IN CAPSULES

(71) Applicant: Capsugel Belgium NV, Bornem (BE)

(72) Inventors: Michael Mark Morgen, Bend, OR (US); Aaron Keith Goodwin, Bend, OR (US)

(73) Assignee: Capsugel Belgium NV, Bornem (BE)

( * ) Notice: Subject to any disclaimer, the term of this patent is extended or adjusted under 35 U.S.C. 154(b) by 418 days.

(21) Appl. No.: 15/579,556

(22) PCT Filed: May 26, 2016

(86) PCT No.: PCT/IB2016/053085
§ 371 (c)(1),
(2) Date: Dec. 4, 2017

(87) PCT Pub. No.: WO2016/198983
PCT Pub. Date: Dec. 15, 2016

(65) Prior Publication Data
US 2018/0161269 A1    Jun. 14, 2018

Related U.S. Application Data

(60) Provisional application No. 62/173,133, filed on Jun. 9, 2015.

(51) Int. Cl.
*A61K 9/00* (2006.01)
*A61K 9/16* (2006.01)
(Continued)

(52) U.S. Cl.
CPC .......... *A61K 9/0004* (2013.01); *A61K 9/1652* (2013.01); *A61K 9/485* (2013.01); *A61K 9/4858* (2013.01); *A61K 31/4166* (2013.01)

(58) Field of Classification Search
None
See application file for complete search history.

(56) References Cited

U.S. PATENT DOCUMENTS 4,758,427 A    7/1988    Leeson
5,972,381 A    10/1999   Sangekar et al.
(Continued)

FOREIGN PATENT DOCUMENTS

CA    2987867      12/2016
EP    0224257 A1   6/1987
(Continued)

OTHER PUBLICATIONS

ECMDB, Mannitol, pp. 1-14, 2015 ([retrieved from on-line website: http://ecmdb.ca/compounds/ECMDB00765, access date: Jul. 5, 2018]). (Year: 2015).*
(Continued)

*Primary Examiner* — Kyung S Chang
(74) *Attorney, Agent, or Firm* — Klarquist Sparkman, LLP (57) ABSTRACT

Disclosed are dosage forms comprising a capsule and a fill material, comprising (a) a fill material comprising a dispersion of an active agent and a polymer, the dispersion being granulated, (b) an osmogen, and (c) a glidant. In one embodiment, the dispersion comprises 10 wt % to 90 wt % of the fill material, the osmogen comprises from 5 wt % to 40 wt % of the fill material, and the glidant comprises at least 0.1 wt % of the fill material.

12 Claims, 2 Drawing Sheets

(51) Int. Cl.
*A61K 9/48* (2006.01)
*A61K 31/4166* (2006.01)

(56) References Cited

U.S. PATENT DOCUMENTS

| | | |
|---|---|---|
| 6,197,781 B1 | 3/2001 | Guitard et al. |
| 6,485,743 B1 | 11/2002 | Jung et al. |
| 6,632,455 B2 | 10/2003 | Sangekar et al. |
| 6,706,283 B1 | 3/2004 | Appel et al. |
| 6,763,607 B2 | 7/2004 | Beyerinck et al. |
| 6,881,745 B2 | 4/2005 | Hayes et al. |
| 6,899,899 B2 | 5/2005 | Takagi et al. |
| 7,235,260 B2 | 6/2007 | Crew et al. |
| 7,605,180 B2 | 10/2009 | Ninomiya et al. |
| 7,704,948 B2 | 4/2010 | Prater et al. |
| 7,780,988 B2 | 8/2010 | Beyerinck et al. |
| 7,897,175 B2 | 3/2011 | Friesen et al. |
| 7,947,670 B2 | 5/2011 | Austad et al. |
| 7,994,214 B2 | 8/2011 | Holm |
| 8,227,463 B2 | 7/2012 | Sugama et al. |
| 8,236,328 B2 | 8/2012 | Babcock et al. |
| 8,257,741 B2 | 9/2012 | Curatolo et al. |
| 8,409,560 B2 | 4/2013 | Padval et al. |
| 8,663,658 B2 | 3/2014 | Park et al. |
| 8,828,438 B2 | 9/2014 | Friesen et al. |
| 2001/0053778 A1 | 12/2001 | Hoover et al. |
| 2002/0031547 A1 | 3/2002 | Takagi et al. |
| 2002/0058065 A1 | 5/2002 | Guivarc'h et al. |
| 2003/0077322 A1 | 4/2003 | Lee |
| 2003/0185891 A1* | 10/2003 | Crew ................ A61P 3/10 424/486 |
| 2003/0198674 A1 | 10/2003 | Curatolo et al. |
| 2003/0228358 A1 | 12/2003 | Perlman et al. |
| 2004/0185102 A1 | 9/2004 | Friesen et al. |
| 2005/0038111 A1 | 2/2005 | Bateman et al. |
| 2005/0163855 A1 | 7/2005 | Cho et al. |
| 2006/0078609 A1 | 4/2006 | Vandecruys et al. |
| 2007/0026072 A1 | 2/2007 | Olsen et al. |
| 2007/0287719 A1 | 12/2007 | Boyden et al. |
| 2008/0227855 A1 | 9/2008 | Buckton et al. |
| 2009/0143423 A1 | 6/2009 | Schroeder et al. |
| 2009/0297565 A1 | 12/2009 | Müller et al. |
| 2009/0311325 A1 | 12/2009 | Janssens et al. |
| 2009/0318500 A1 | 12/2009 | Trewartha et al. |
| 2010/0015225 A1 | 1/2010 | Diederich et al. |
| 2010/0112052 A1* | 5/2010 | Chen ................ A61K 9/0004 424/468 |
| 2011/0002989 A1 | 1/2011 | Curatolo et al. |
| 2011/0189297 A1 | 8/2011 | Ludtke et al. |
| 2011/0207804 A1 | 8/2011 | Beijnen et al. |
| 2012/0064157 A1 | 3/2012 | Dokou et al. |
| 2012/0077835 A1 | 3/2012 | Selbo et al. |
| 2013/0149346 A1 | 6/2013 | Meergans et al. |
| 2014/0100256 A1 | 4/2014 | Lorenz et al. |
| 2014/0148449 A1 | 5/2014 | Bi et al. |
| 2014/0271842 A1* | 9/2014 | Herbig ................ A61P 19/02 424/457 |
| 2014/0288037 A1 | 9/2014 | Casebier et al. |
| 2014/0296267 A1* | 10/2014 | Fry ................ A61K 9/2009 514/266.21 |
| 2015/0011525 A1 | 1/2015 | Bi et al. |
| 2015/0018353 A1* | 1/2015 | Kim ................ C07D 413/14 514/236.5 |
| 2015/0216813 A1 | 8/2015 | Everett et al. |

FOREIGN PATENT DOCUMENTS

| | | |
|---|---|---|
| EP | 1039908 B1 | 2/2004 |
| EP | 0954288 B1 | 8/2004 |
| EP | 0901786 B1 | 6/2007 |
| EP | 1920766 A2 | 5/2008 |
| EP | 1027886 B1 | 7/2008 |
| EP | 1027887 B1 | 8/2008 |
| EP | 2197425 A2 | 6/2010 |
| EP | 2739269 A2 | 6/2014 |
| EP | 3307246 | 4/2018 |
| FR | 2327764 A1 | 5/1977 |
| IN | 2008CH02491 A | 10/2010 |
| JP | 2013536251 | 9/2013 |
| JP | 2014507424 | 3/2014 |
| JP | 2014528484 | 10/2014 |
| JP | 2016505029 A | 2/2016 |
| JP | 2017500343 A | 1/2017 |
| JP | 2018516900 A | 6/2018 |
| KR | 100555794 B1 | 3/2006 |
| KR | 20140050876 A | 4/2014 |
| WO | WO2007/024123 A1 | 3/2007 |
| WO | WO2007/040306 A1 | 4/2007 |
| WO | WO2007/141806 A1 | 12/2007 |
| WO | WO2010/102245 A1 | 9/2010 |
| WO | WO2012/027731 | 3/2012 |
| WO | WO2012/122279 | 9/2012 |
| WO | WO2013/056108 | 4/2013 |
| WO | WO2013/169523 A1 | 11/2013 |
| WO | WO2014/042945 | 3/2014 |
| WO | WO2014/087106 A1 | 6/2014 |
| WO | WO2014/114575 | 7/2014 |
| WO | WO2014/170026 A1 | 10/2014 |
| WO | WO2015/095659 A2 | 6/2015 |

OTHER PUBLICATIONS

Al-Tabakha M M, "HPMC capsules: current status and future prospects", J Pharm Pharm Sci. 2010; 13(3):428-42 (Year: 2010).*
Office Action for European Patent Application No. 16728108.8, mailed Jun. 14, 2019.
Office Action for Japanese Patent Application No. 2017-559653, mailed Mar. 9, 2020.
Office Action for European Patent Application No. 16728108.8, mailed Aug. 8, 2020.
Office Action for European Patent Application No. 16728108.8, mailed Aug. 18, 2021.
International Search Report and Written Opinion for PCT/IB2016/053085, mailed Jul. 25, 2016.

* cited by examiner

FORMULATIONS TO ACHIEVE RAPID DISSOLUTION OF DRUG FROM SPRAY-DRIED DISPERSIONS IN CAPSULES

CROSS REFERENCE TO RELATED APPLICATIONS

This is the U.S. National Stage of International Application No. PCT/IB2016/053085, filed May 26, 2016, which was published in English under PCT Article 21(2), which in turn claims the benefit of U.S. Provisional Application No. 62/173,133, filed Jun. 9, 2015; both of which are incorporated herein in their entireties.

TECHNICAL FIELD

Disclosed are dosage forms comprising a dispersion of a drug, a polymer, an osmogen, and a glidant, wherein said compositions result in rapid release of the dispersion upon administration to an aqueous use environment.

BACKGROUND

Rapid release of spray dried dispersions when filled into a capsule is desirable. However, when the capsule enters an aqueous use environment, including in vivo or in vitro use environments, the dispersion imbibes water, leading to wetting and/or gelation of the dispersion polymer, while it is in prolonged confinement within the capsule. This can lead to poor dispersal and/or dissolution of drug from the formulation once the capsule dissolves. This challenge is particularly evident for amphiphilic polymers that are capable of hydrogel formation, including substituted cellulosics such as HPMC and HPMCAS. Essentially, the water ingress into the capsule causes gelling of the dispersion polymer before the capsule shell can completely dissolve, resulting in slow dispersing or dissolution of the spray dried dispersion (SDD) particles into the aqueous use environment after the capsule dissolves.

SUMMARY

In one embodiment, a dosage form comprises a capsule and a fill material, the fill material comprising (a) a dispersion of an active agent and a polymer, the dispersion being granulated, (b) an osmogen, and (c) a glidant. In one embodiment, the dispersion comprises 10 wt % to 90 wt % of the fill material, the osmogen comprises from 5 wt % to 40 wt % of the fill material, and the glidant comprises at least 0.1 wt % of the fill material.

The invention involves the use of an osmogen, such as small, highly water soluble excipients, to reduce wetting and/or gelling of the dispersion-containing particles within a capsule formulation. Mechanistically, it is believed that the small excipients—for example, a highly water-soluble inorganic salt, sugar or sugar alcohol—quickly dissolve upon wetting once water begins to penetrate the capsule shell, lowering the water activity of the aqueous use media in contact with the dispersion-containing particles. Adding such an osmogen to the fill material decreases the water activity within the capsule once the capsule has been administered to an aqueous use environment (such as an in vitro test media or in vivo in the gastrointestinal tract of an animal). The resulting highly concentrated solution inside the capsule interior is of a nature that the dispersion particles are not well wetted by the solution or highly swollen by water within the pre-dissolved capsule. This prevents gelation of the dispersion particles, and allows rapid dispersal of the dispersion particles upon complete dissolution of the capsule shell. Simultaneously, granulating the dispersion into larger particles reduces the surface area per unit mass of the dispersion, and also reduces the propensity of the dispersion to gel.

In one embodiment, the dispersion comprises 20 wt % to 90 wt % of the fill material. In still another embodiment, the dispersion comprises at least 20 wt % of the fill material, at least 30 wt % of the fill material, at least 40 wt % of the fill material, at least 50 wt % of the fill material, at least 60 wt % of the fill material, at least 70 wt % of the fill material, or even at least 80 wt % of the fill material.

In one embodiment, the osmogen is selected from the group consisting of magnesium chloride, magnesium sulfate, lithium chloride, sodium chloride, potassium chloride, lithium hydrogen phosphate, sodium hydrogen phosphate, potassium hydrogen phosphate, lithium dihydrogen phosphate, sodium dihydrogen phosphate, potassium dihydrogen phosphate, trehalose, glucose, sucrose, maltose, xylitol, mannitol, sorbitol, and combinations thereof. In still another embodiment, the osmogen is selected from the group consisting of sorbitol, sodium chloride, potassium chloride, xylitol, or combinations thereof. In one embodiment, the osmogen comprises 10 wt % to 35 wt % of the fill material. In another embodiment, the osmogen comprises 15 wt % to 30 wt % of the fill material. In another embodiment the osmogen comprises at least 10 wt % of the fill material, at least 15 wt % of the fill material, at least 20 wt % of the fill material.

In one embodiment, the glidant is selected from the group consisting of silica, fumed silica, silicon dioxide, aerosil, magnesium aluminosilicates, magnesium aluminometasilicates, and mixtures thereof.

In still another embodiment the dispersion and osmogen are co-granulated prior to being placed in the capsule. In still another embodiment the dispersion and osmogen are subjected to high-shear mixing prior to being placed in the capsule. In another embodiment, the dispersion and glidant are co-granulated prior to being placed in the capsule. In one embodiment, the dispersion is granulated, then blended with the osmogen and glidant.

In one embodiment, the osmogen comprises from 10 wt % to 35 wt % of the fill material. In other embodiments, the osmogen comprises from 15 wt % to 35 wt % of the fill material. In still another embodiment, the osmogen comprises from 20 wt % to 35 wt % of the fill material. In still another embodiment, the osmogen comprises from 30 wt % to 35 wt % of the fill material.

In one embodiment the glidant comprises from 0.5 wt % to 5 wt % of the fill material. In still another embodiment, the glidant comprises from 1 wt % to 5 wt % of the fill material. In another embodiment, the glidant comprises from 1 wt % to 3 wt % of the fill material.

In another embodiment the osmogen comprises from 5 wt % to 70 wt % of the fill material. In another embodiment the osmogen comprises from greater than 40 wt % to 70 wt % of the fill material. In another embodiment, the osmogen comprises from 50 wt % to 70 wt % of the fill material. In another embodiment the osmogen comprises 60 wt % to 70 wt % of the fill material. In one embodiment, the dosage form consists essentially of a capsule and a fill material, the fill comprising (a) a dispersion of an active agent and a polymer, the dispersion being granulated, (b) an osmogen, and (c) a glidant. In another embodiment, the dosage form consists of a capsule and a fill material, the fill comprising (a) a dispersion of an active agent and a polymer, the dispersion being granulated, (b) an osmogen, and (c) a glidant.

DETAILED DESCRIPTION

The inventors have identified a continuing need to develop methods and compositions to improve the bioavailability of active agents. In one embodiment, the dosage form comprises a capsule and a fill material, the fill material comprising (a) a dispersion of an active agent and a polymer, the dispersion being granulated, (b) an osmogen, and (c) a glidant.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

Unless otherwise indicated, all numbers expressing quantities of ingredients, properties such as molecular weight, percentages, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Dispersions of an Active Agent and a Polymer

Embodiments of the disclosed compositions comprise dispersions comprising an active agent and a dispersion polymer. In one embodiment, the compositions comprise a solid amorphous dispersion. One reason for forming solid amorphous dispersion is that the aqueous dissolved active agent concentration of a poorly aqueous soluble active agent may be improved by forming an amorphous dispersion of the active agent and a polymer. Such solid amorphous dispersions of drug and polymer provide higher concentrations of dissolved drug in an aqueous solution compared with the drug in crystalline form. Such solid amorphous dispersions tend to perform best when the drug is homogeneously dispersed throughout the polymer, thus in one embodiment, the compositions comprise a homogenous solid amorphous dispersion, i.e. a solid solution. In one embodiment, the compositions are in the form of a solid dispersion of the active agent and the polymer, wherein at least 75 wt % of the active agent in the dispersion is non-crystalline. In another embodiment, at least 90 wt % of the active agent is in the form of a solid solution in the dispersion. In still another embodiment, essentially all of the active agent is in a non-crystalline form. In one embodiment, the dispersion is comprises a solid solution of the active agent in the dispersion polymer. By "non-crystalline" is meant that the is meant that the active agent "amorphous" as determined by differential scanning calorimetry (DSC), powder X-ray diffraction (PXRD), by solid state nuclear magnetic resonance (NMR), or by any other known quantitative measurement. A dispersion is considered a "solid solution" when it displays a single Tg when analyzed by differential scanning calorimetry. In one embodiment, the dispersions have at least one Tg due to the amorphous character of the polymer. In another embodiment, essentially all of the active agent and the polymer in the dispersion are in the form of a solid solution. In one embodiment, the composition consists essentially of a solid solution of the active agent and the polymer.

In another embodiment, the dispersion comprises two or more active agents.

The solid dispersions of the present invention may be formed by any method known in the art, including milling, extrusion, precipitation, or solvent addition followed by solvent removal. For example, active agent and the polymer may be processed by heat, mechanical mixing and extrusion using, for example, a twin-screw extruder. The product may then be milled to the desired particle size. In another example, the active agent and polymer are dissolved in a solvent in which both materials are soluble. The dispersions may then be formed from the solution by any known process, including precipitation in a miscible non-solvent, emulsifying in an immiscible non-solvent, or by forming droplets followed by removal of the solvent by evaporation.

In one embodiment, the solid dispersion is formed by spray drying. The active agent, the dispersion polymer, and optional excipients may be dissolved in a solvent. Thus, the fluid that is spray dried may be a suspension or a homogeneous solution or a combination of dissolved and suspended materials. In one embodiment, the fluid that is spray dried comprises a homogeneous solution of active agent and dispersion polymer dissolved together in a solvent. In another embodiment, the fluid that is spray dried consists essentially of a solution of active agent and polymer dissolved in a solvent. In still another embodiment, the fluid that is spray dried comprises a suspension of active agent particles in a solution of polymer dissolved in a solvent. In still another embodiment, the active agent and polymer, wherein said at least one of the active agent and the polymer is suspended in said solvent, is directed to a heat exchanger to form a spray solution, in which both the active agent and polymer are dissolved, as disclosed in pending patent application WO2010111132 A2, incorporated herein by reference.

In one embodiment, the dosage form consists essentially of a capsule and a fill material, the fill material consisting essentially of (a) a dispersion of an active agent and a polymer, the dispersion being granulated, (b) an osmogen, and (c) a glidant. In another embodiment, the dosage form consists of a capsule and a fill material, the fill material consisting of (a) a dispersion of an active agent and a polymer, the dispersion being granulated, (b) an osmogen, and (c) a glidant.

Active Agents

Embodiments of the disclosed compositions are suitable for use with any biologically active compound desired to be administered to a patient in need of the active agent. The compositions may contain one or more active agents. As used herein, by "active" or "active agent" is meant a drug, medicament, pharmaceutical, therapeutic agent, nutraceutical, or other compound that may be desired to be administered to the body. The active is generally a "small molecule," having a molecular weight of 2000 Daltons or less. The compositions may also include a mixture two or more active agents.

The active agent should be understood to include the non-ionized form of the active as well as the ionized form of the active. By non-ionized form is meant that the active is not converted to an ionic form. By ionized form is meant that at least one pH in the physiological pH range of 1-8, the active is converted to an ionic form, i.e., a cation or anion. In one embodiment, the active includes pharmaceutically acceptable forms of the active. The term "pharmaceutically acceptable" refers to a substance that can be taken into a subject without significant adverse toxicological effects on the subject. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, and prodrugs of the active.

Examples of classes of active agents include, but are not limited to, compounds for use in the following therapeutic areas: antihypertensives, antianxiety agents, antiarrhythmia agents, anticlotting agents, anticonvulsants, blood glucose-lowering agents, decongestants, antihistamines, antitussives, antineoplastics, anticancer agents, antitumor agents, beta blockers, anti-inflammatories, antipsychotic agents, cognitive enhancers, anti-atherosclerotic agents, cholesterol-reducing agents, triglyceride-reducing agents, antiobesity agents, autoimmune disorder agents, anti-impotence agents, antibacterials, anthelmintics, antihelminthics, antifungal agents, hypnotic agents, anti-Parkinsonism agents, anti-Alzheimer's disease agents, antibiotics, anti-angiogenesis agents, anti-glaucoma agents, anti-depressants, anti-acne agents, bronchodilators, glucocorticoids, steroids, and antiviral agents.

Dispersion Polymers

Exemplary dispersion polymers include cellulose, ethylcellulose (EC), propylcellulose, butylcellulose, cellulose acetate (CA), cellulose propionate, cellulose butyrate, cellulose acetate butyrate (CAB), cellulose acetate propionate, methyl cellulose acetate, methyl cellulose propionate, methyl cellulose butyrate, ethyl cellulose acetate, ethyl cellulose propionate, ethyl cellulose butyrate, hydroxypropyl methyl cellulose (HPMC), hydroxypropyl methylcellulose acetate (HPMCA), dextran acetate, dextran propionate, dextran acetate propionate, dextran succinate, polyvinyl caprolactam, polyvinyl acetate, polyoxyethylene castor oils, polycaprolactam, polylactic acid, polyvinylpyrrolidone (PVP), vinyl acetate/vinylpyrrolidone copolymers (PVPVA), polyglycolic acid, poly(lactic-glycolic)acid, hydroxypropyl methyl cellulose acetate succinate (HPMCAS), hydroxypropyl methyl cellulose propionate succinate, hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, carboxymethyl ethylcellulose (CMEC), hydroxypropyl methylcellulose acetate phthalate (HPMCAP), hydroxypropyl methylcellulose propionate phthalate, hydroxypropyl methylcellulose acetate trimellitate (HPMCAT), carboxymethyl cellulose acetate butyrate (CMCAB), hydroxypropyl methylcellulose propionate trimellitate, cellulose acetate succinate (CAS), methyl cellulose acetate succinate (MCAS), dextran acetate succinate, dextran propionate succinate, dextran acetate propionate succinate, poly(methacrylic acid-co-methyl methacrylate) 1:1 (e.g., Eudragit® L100, Evonik Industries AG), poly(methacrylic acid-co-methyl methacrylate) 1:2 (e.g., Eudragit® S100), poly(methacrylic acid-co-ethyl acrylate) 1:1 (e.g., Eudragit® L100-55), poloxamers, poly(ethylene oxide-b-ε-caprolactone), poly(ε-caprolactone-b-ethylene glycol), poly(ethylene oxide-b-lactide), poly(lactide-b-ethylene glycol), poly(ethylene oxide-b-glycolide), poly(glycolide-b-ethylene glycol), poly(ethylene oxide-b-lactide-co-glycolide), poly(lactide-co-glycolide-b-ethylene glycol), and mixtures thereof.

In one embodiment, the dispersion polymer is selected from hydroxypropyl methyl cellulose (HPMC), hydroxypropyl methylcellulose acetate (HPMCA), dextran acetate, dextran propionate, dextran acetate propionate, polyvinyl caprolactam, polyvinyl acetate, polyoxyethylene castor oils, polycaprolactam, polylactic acid, polyglycolic acid, poly (lactic-glycolic)acid, hydroxypropyl methyl cellulose acetate succinate (HPMCAS), hydroxypropyl methyl cellulose propionate succinate, hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, carboxymethyl ethylcellulose (CMEC), hydroxypropyl methylcellulose acetate phthalate (HPMCAP), hydroxypropyl methylcellulose propionate phthalate, hydroxypropyl methylcellulose acetate trimellitate (HPMCAT), carboxymethyl cellulose acetate butyrate (CMCAB), hydroxypropyl methylcellulose propionate trimellitate, cellulose acetate succinate (CAS), methyl cellulose acetate succinate (MCAS), dextran acetate succinate, dextran propionate succinate, dextran acetate propionate succinate, and mixtures thereof.

In one embodiment, the dispersion polymer is selected from the group consisting of HPMCAS, HPMC, PVPVA, PVP, poly(methacrylic acid-co-methyl methacrylate), poly (methacrylic acid-co-methyl methacrylate), poly(methacrylic acid-co-ethyl acrylate), and CAP.

In another embodiment, the dispersion polymer is selected from the group consisting of HPMCAS, HPMC, and PVPVA.

In another embodiment, the dispersion polymer is selected from the group consisting of HPMCAS, and HPMC.

In another embodiment, the dispersion polymer is HPMCAS.

In another embodiment, the dispersion polymer is selected from the group consisting of poly(methacrylic acid-co-methyl methacrylate), poly(methacrylic acid-co-methyl methacrylate), and poly(methacrylic acid-co-ethyl acrylate).

Osmogens

The compositions of the invention also comprise an osmogen, typically comprising from 5 wt % to 40 wt % of the fill material. Exemplary osmogens include salts such as magnesium chloride, magnesium sulfate, lithium chloride, sodium chloride, potassium chloride, lithium hydrogen phosphate, sodium hydrogen phosphate, potassium hydrogen phosphate, lithium dihydrogen phosphate, sodium dihydrogen phosphate, potassium dihydrogen phosphate, potassium sulfate, sodium carbonate, sodium sulfite, lithium sulfate, calcium carbonate, sodium sulfate, calcium sulfate, calcium lactate, magnesium succinate; solid alcohols and sugar alcohols, such as trehalose, glucose, sucrose, raffinose, maltose, xylitol, mannitol, sorbitol, glycerol, lactitol, maltitol and erythritol; as well as urea, inositol, tartaric acid, and combinations thereof. In still another embodiment the osmogen is selected from sorbitol, xylitol, sodium chloride, potassium chloride, and mixtures thereof.

In other embodiments, the osmogen comprises from 10 wt % to 35 wt % of the fill material. In other embodiments, the osmogen comprises from 15 wt % to 35 wt % of the fill material. In still another embodiment, the osmogen comprises from 20 wt % to 35 wt % of the fill material. In still another embodiment, the osmogen comprises from 30 wt % to 35 wt % of the fill material.

In one embodiment, the osmogen has a low molecular weight. The osmogen may have a molecular weight of less than 500 Daltons, less than 350, Dalton, or less than 200 Daltons.

In another embodiment, the osmogen has a high water solubility, expressed as the molality (moles of solute per unit mass) of a saturated solution (mol/kg). Preferably the osmogen has a water solubility of greater than 1 mol/kg, more preferably at least 2.5 mol/kg, and even more preferably at least 4 mol/kg.

In another embodiment, the osmogen has both a low molecular weight and high water solubility. Thus, the osmogen may have a molecular weight of less than 500 Da and a water solubility of at least 1 mol/kg, may have a molecular weight of less than 350 Da and a water solubility of at least 2.5 mol/kg, or may have a molecular or formula weight of less than 200 mol/kg and a water solubility of at least 4 mol/kg.

Table 1 lists the molecular weight and molality of several osmogens.

TABLE 1

| Osmogen | MW (Da) | Water Solub. (mol/kg) |
|---|---|---|
| lactose | 342 | 0.58 |
| mannitol | 182 | 0.99 |
| maltose | 342 | 2.63 |
| fructose | 180 | 3.89 |
| xylitol | 152 | 4.11 |
| sorbitol | 182 | 4.56 |
| KCl | 74 | 9.40 |
| NaCl | 58 | 12.32 |

A preferred list of osmogens is magnesium chloride, magnesium sulfate, lithium chloride, sodium chloride, potassium chloride, lithium hydrogen phosphate, sodium hydrogen phosphate, potassium hydrogen phosphate, sodium dihydrogen phosphate, potassium dihydrogen phosphate, potassium sulfate, sodium carbonate, sodium sulfite, lithium sulfate, sodium sulfate, trehalose, glucose, sucrose, maltose, xylitol, sorbitol, urea, tartaric acid, lactitol, maltitol, erythritol and combinations thereof.

A more preferred list of osmogens is sodium chloride, potassium chloride, xylitol, and sorbitol.

Glidants

The compositions also include a glidant, typically comprising at least 0.1 wt % of the fill material. Exemplary glidants include silica, silicon dioxide, aerosol, magnesium aluminosilicates, magnesium aluminometasilicates, starch, talc, micro crystalline cellulose, magnesium carbonate, magnesium trisilicate, tribasic calcium phosphate, leucine, titanium dioxide, and mixtures thereof. In one embodiment, the glidant is selected from silica (e.g., Syloid®), fumed silica (e.g., Aerosil® by Evonik, or Cab-O-Sil® by Cabot), silicon dioxide, magnesium aluminometasilicates (e.g., Neusilin®), magnesium aluminosilicates, titanium dioxide, and mixtures thereof. In one embodiment the glidant comprises from 0.5 wt % to 5 wt % of the fill material. In still another embodiment, the glidant comprises from 1 wt % to 5 wt % of the fill material. In another embodiment, the glidant comprises from 1 wt % to 3 wt % of the fill material.

Capsules

The compositions of the present invention may be filled into any commercially available capsule, such as gelatin capsules, hydroxypropyl methylcellulose (HPMC) capsules, capsules made from other materials such as pullulan, starch, and pectin, enteric capsules, and other capsules well known in the art. Exemplary capsules include Vcaps®, Vcaps Plus®, Licaps®, OceanCaps™, DBcaps®, PCcaps®, ConiSnap®, DRcaps™ OceanCaps®, Pearlcaps®, Plantcaps®, SGcaps®, or other capsules known in the art.

In one preferred embodiment, the capsule is an HPMC capsule.

In another preferred embodiment, the capsule is an HPMC capsule and the dispersion polymer is selected from the group consisting of HPMCAS, HPMC, PVPVA, PVP, poly(methacrylic acid-co-methyl methacrylate), poly(methacrylic acid-co-methyl methacrylate), poly(methacrylic acid-co-ethyl acrylate), and CAP.

Methods of Preparing the Compositions

In one embodiment, the dispersion of an active agent and a polymer is granulated prior to adding the osmogen and the glidant. Granulation techniques include dry granulation, wet granulation, fluidized bed granulation, and other processes known in the art. Examples of dry granulation include slugging, or using a roller compactor to produce ribbons, which are then milled to reduce the particle size. Dry granulation may also include high-shear mixer-granulators. Granulation may also be conducted in an extruder. Wet granulation may also be used to granulate the materials, often including a liquid that is volatile so it can be removed following the wet granulation process. Fluidized bed granulation may also be included in the wet granulation process.

Typically, the granulated materials are milled to the desired particle size using an appropriate milling procedure.

Once the granules are appropriately sized, they may be blended with the osmogen and filled into the capsule, either without tamping, or lightly tamped or compressed during the filling process, using e.g. a tamping pin or dosator filling technique. Typically, the glidant is blended with the granulation and osmogen.

In one embodiment, the dispersion may be granulated with the osmogen, using similar techniques as described above. The glidant may then be mixed with the granules and filled into the capsule with no tamping or lightly tamped or compressed as described above.

In one embodiment, the dispersion may be granulated with the glidant present, using similar techniques as described above. The osmogen may then be mixed with the granules and filled into the capsule, with no tamping or lightly tamped or compressed as described above.

Methods of Use

In one embodiment, the disclosed compositions are intended for administration to an animal via a mode selected from oral, buccal, mucosal, sublingual, or combinations thereof.

Conventional formulation excipients may be employed in embodiments of the disclosed compositions, including those excipients well-known in the art, such as those described in Remington: The Science and Practice of Pharmacy (20th ed., 2000). Generally, excipients such as fillers, disintegrating agents, pigments, binders, lubricants, glidants, flavorants, and so forth may be used for customary purposes and in typical amounts without adversely affecting the properties of the compositions.

When placed into an aqueous environment of use, the capsules rapidly release the spray dried dispersion into the use environment. In one embodiment, the capsules release active agent such that the solubilized active concentration in the disso media after 30 minutes in simulated gastric fluid is at least 50%, 75%, 80%, 90%, or 100% of the concentration provided by an SDD tested as an unencapsulated suspension using the same protocol, e.g. the test method of Example 1. In another embodiment, the capsules release active agent such that the solubilized active concentration in the disso media after 10, 20, 40, or 90 minutes in simulated intestinal fluid at pH 6.5 is at least 50%, 75%, 80%, 90%, or 100% of the concentration provided by an SDD tested as an unencapsulated suspension using the same protocol, e.g. the test method of Example 1. In another embodiment, the composition of the invention releases active agent such that the solubilized active concentration in a dissolution test (e.g. described in Example 1) is at least 25%, 50%, 75%, or 100% more than that provided by a control formulation comprising only the similar capsule and a fill consisting of the dispersion. of the active agent.

In one embodiment, a dosage form comprising a capsule and a fill material, comprises (a) a fill material comprising a dispersion of an active agent and a polymer the dispersion being granulated, (b) an osmogen, and (c) a glidant. In one embodiment, the dispersion comprises 10 wt % to 90 wt % of the fill material, the osmogen comprises from 5 wt % to 40 wt % of the fill material, and the glidant comprises at least 0.1 wt % of the fill material. In another embodiment, the dispersion comprises 20 wt % to 90 wt % of the fill material. In still another embodiment, the dispersion comprises at least 20 wt % of the fill material, at least 30 wt % of the fill material, at least 40 wt % of the fill material, at least 50 wt % of the fill material, at least 60 wt % of the fill material, at least 70 wt % of the fill material, or even at least 80 wt % of the fill material.

In one embodiment, the osmogen comprises from 10 wt % to 35 wt % of the fill material. In other embodiments, the osmogen comprises from 15 wt % to 35 wt % of the fill material. In still another embodiment, the osmogen comprises from 20 wt % to 35 wt % of the fill material. In still another embodiment, the osmogen comprises from 30 wt % to 35 wt % of the fill material.

In another embodiment the osmogen comprises from 5 wt % to 70 wt % of the fill material. In another embodiment the osmogen comprises from greater than 40 wt % to 70 wt % of the fill material. In another embodiment the osmogen comprises from 50 wt % to 70 wt % of the fill material. In another embodiment the osmogen comprises 60 wt % to 70 wt % of the fill material.

In one embodiment, the glidant comprises at least 0.1 wt % of the fill material. In one embodiment the glidant comprises from 0.5 wt % to 5 wt % of the fill material. In still another embodiment, the glidant comprises from 1 wt % to 5 wt % of the fill material. In another embodiment, the glidant comprises from 1 wt % to 3 wt % of the fill material.

EXAMPLES

In all examples, a dispersion of phenytoin and the H-grade (as designated by Shin Etsu chemical) of hydroxypropyl methyl cellulose acetate succinate (HPMCAS, also known as hypromellose acetate succinate) was used. The dispersion was a homogeneous dispersion and contained 25 wt % phenytoin, i.e. 25% wt. phenytoin, 75% wt. HPMCAS-H After evaluating by powder X-ray diffraction, there was no evidence of crystalline material in the formulations.

Example 1

SDD with Sorbitol

In this example, the 25 wt % Phenytoin:HPMCAS-H SDD was used. The SDD was first granulated by slugging the SDD powder and compressing to a solid fraction of 0.66. The slugs were then milled using a mortar and pestle, and passed through a 30 mesh screen. The granules were then mixed with the extra-granular materials in a Turbula blender for 20 minutes at 32 rpm. The composition of the capsule fill material is given in the following table.

| Component | Material Class | Amount (wt %) |
| --- | --- | --- |
| Granulation | | |
| SDD | dispersion of active and polymer | 66.67 |
| Extra-granular | | |
| Sorbitol | Osmogen | 31.33 |
| Neuslin ® | Glidant | 2.00 |
| TOTAL | | 100.00 |

The formulation was then filled into size 00 HPMC (Vcaps® Plus) capsules, without tamping. Each capsule contained 300 mg of the formulation.

Figure 1:
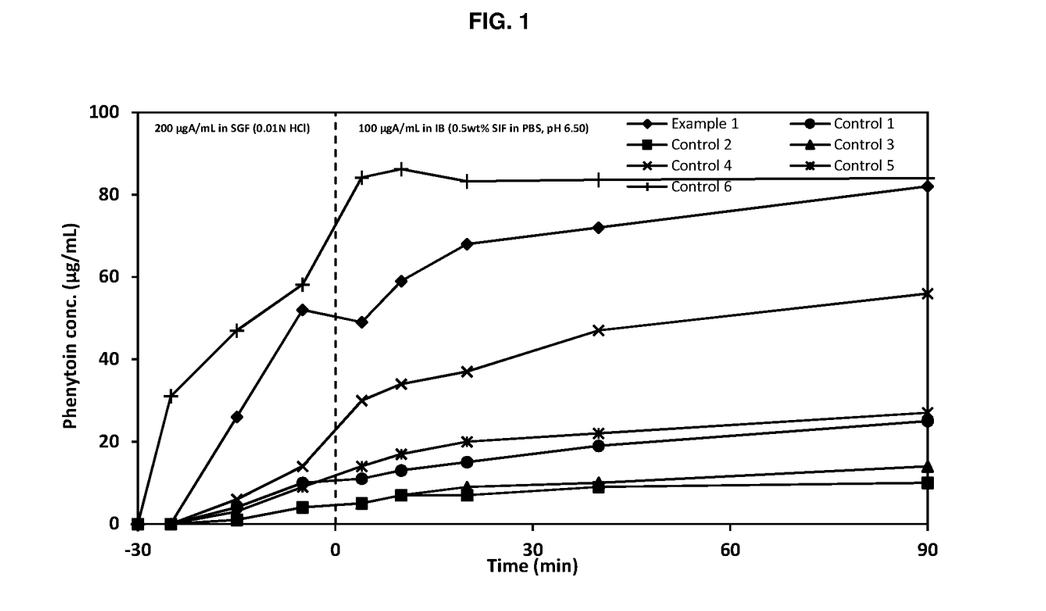
FIG. 1-3 show the results of dissolution tests on the compositions in the Examples.
Figure 2:
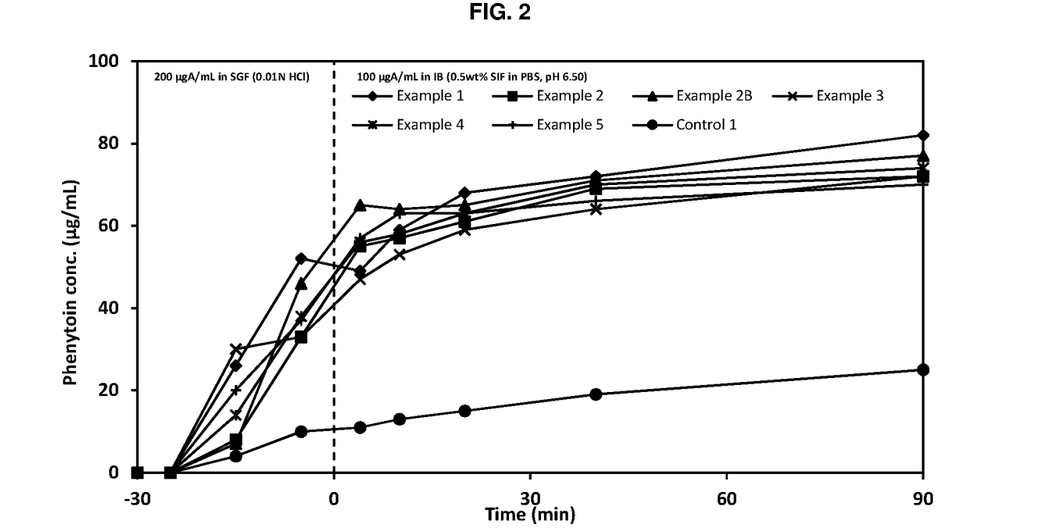
Figure 3:
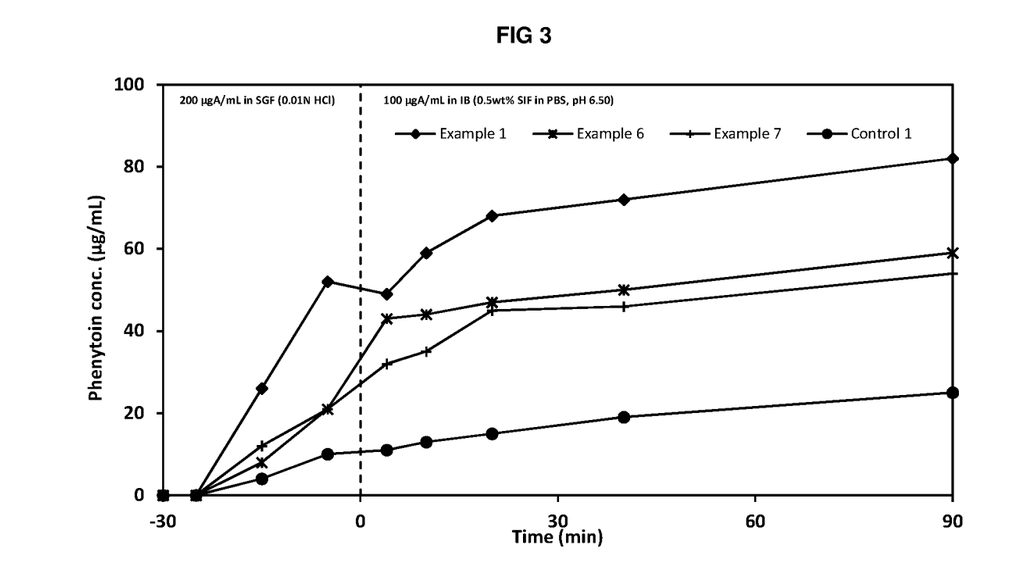

The filled capsule of Example 1 was dissolution tested using the following procedure. The capsule was placed with a sinker to prevent floating. The capsule was first placed in 250 mL simulated gastric media (0.01 N HCl) in a 500 mL USP II dissolution apparatus stirred at 75 RPM. Samples were collected at 5, 15, and 25 minutes centrifuged @ 15,800 g for 1 minute and the supernatant diluted (50 µL supernatant into 250 µL diluent in HPLC vials) and analyzed by HPLC at a later time. Next, 250 mL of intestinal buffer media was added resulting in simulated intestinal fluid consisting of 0.5 wt % SIF powder (from Biorelevant.com) in phosphate buffered saline at pH 6.5. Samples were collected at 4, 10, 20, 40, and 90 minutes and analyzed by HPLC using the same techniques. The results are shown in FIG. 1, 2, 3.

Example 2

SDD with Sodium Chloride (NaCl)

The SDD of Example 1 was used in this example. The SDD was first granulated by slugging the SDD powder and compressing to a solid fraction of 0.66. The slugs were then milled using a mortar and pestle, and passed through a 30 mesh screen. The granules were then mixed with the extra-granular materials in a Turbula blender for 20 minutes at 32 rpm. The composition of the capsule fill material is given in the following table.

| Component | Material Class | Amount (wt %) |
|---|---|---|
| Granulation | | |
| SDD | dispersion of active and polymer | 66.67 |
| Extra-granular | | |
| NaCl | Osmogen | 31.33 |
| Neuslin | Glidant | 2.00 |
| TOTAL | | 100.00 |

The formulation was then filled into size 00 HPMC (Vcaps® Plus) capsules, without tamping. Each capsule contained 300 mg of the formulation. The capsule of Example 2 was dissolution tested as described in Example 1. The results are included in FIG. 2.

Example 2B

Granulated SDD with Intragranular NaCl, Extragranular Glidant

The SDD of Example 1 was used in this example. The SDD was mixed with NaCl on a Turbula blender for 20 minutes at 32 rpm, and then granulated by slugging the blend and compressing to a solid fraction of 0.66. The slugs were then milled using a mortar and pestle, and passed through a 30 mesh screen. The granules were then mixed with the extra-granular glidant (Neusilin®) in a Turbula blender for 20 minutes at 32 rpm. The composition of the capsule fill material is given in the following table.

| Component | Material Class | Amount (wt %) |
|---|---|---|
| Granulation | | |
| SDD | dispersion of active and polymer | 66.67 |
| NaCl | Osmogen | 31.33 |
| Extra-granular | | |
| Neusilin ® | Glidant | 2.00 |
| TOTAL | | 100.00 |

The formulation was then filled into 00 HPMC (Vcaps® Plus) capsules, without tamping. Each capsule contained 300 mg of the formulation. The capsule of Example 2B was dissolution tested as described in Example 1. The results are included in FIG. 2.

Example 3

SDD with Xylitol

The SDD of Example 1 was used in this example. The SDD and the glidant were co-screened through a 30-mesh screen, and then mixed for 20 minutes in a Turbula blender. The intra-granular components were then granulated by slugging the mixture and compressing to a solid fraction of 0.66. The slugs were then milled using a mortar and pestle, and passed through a 30 mesh screen. The granules were then mixed with the extra-granular materials in a Turbula blender for 20 minutes at 32 rpm. The composition of the capsule fill material is given in the following table.

| Component | Material Class | Amount (wt %) |
|---|---|---|
| Intra-granular | | |
| SDD | dispersion of active and polymer | 66.67 |
| Cab-o-sil | Glidant | 1.00 |
| Extra-granular | | |
| Xylitol | Osmogen | 30.33 |
| Neuslin | Glidant | 2.00 |
| TOTAL | | 100.00 |

The formulation was then filled into size 00 HPMC (Vcaps® Plus) capsules, without tamping. Each capsule contained 300 mg of the formulation. The capsule of Example 3 was dissolution tested as described in Example 1. The results are included in FIG. 2.

Example 4

SDD with Xylitol

The SDD of Example 1 was used in this example. The SDD was granulated by slugging the SDD powder and compressing to a solid fraction of 0.66. The slugs were then milled using a mortar and pestle, and passed through a 30 mesh screen. The granules were then mixed with the extra-granular materials in a Turbula blender for 20 minutes at 32 rpm. The composition of the capsule fill material is given in the following table.

| Component | Material Class | Amount (wt %) |
|---|---|---|
| Intra-granular | | |
| SDD | dispersion of active and polymer | 66.67 |
| Extra-granular | | |
| Xylitol | Osmogen | 31.33 |
| Neuslin | Glidant | 2.00 |
| TOTAL | | 100.00 |

The formulation was then filled into size 00 HPMC (Vcaps® Plus) capsules, without tamping. Each capsule contained 300 mg of the formulation. The capsule of Example 4 was dissolution tested as described in Example 1. The results are included in FIG. 2.

Example 5

SDD with Intragranular Xylitol, Extragranular Glidant

The SDD of Example 1 was used in this example. The SDD was mixed with xylitol on a Turbula blender for 20 minutes at 32 rpm, and then granulated by slugging the blend and compressing to a solid fraction of 0.66. The slugs were then milled using a mortar and pestle, and passed through a 30 mesh screen. The granules were then mixed with the extra-granular glidant (Neusilin) in a Turbula blender for 20 minutes at 32 rpm. The composition of the capsule fill material is given in the following table.

| Component | Material Class | Amount (wt %) |
|---|---|---|
| Granulation | | |
| SDD | dispersion of active and polymer | 66.67 |
| Xylitol | Osmogen | 31.33 |
| Extra-granular | | |
| Neusilin ® | Glidant | 2.00 |
| TOTAL | | 100.00 |

The formulation was then filled into size 00 HPMC (Vcaps® Plus) capsules, without tamping. Each capsule contained 300 mg of the formulation. The capsule of Example 5 was dissolution tested as described in Example 1. The results are included in FIG. 2.

Example 6

Granulated SDD Blended with Extragranular Mannitol Osmogen and Neusilin® Glidant The SDD of Example 1 was used in this example. The SDD was granulated by slugging it and compressing to a solid fraction of 0.66. The slugs were then milled using a mortar and pestle, and passed through a 30 mesh screen. The granules were then mixed with the extra-granular materials in a Turbula blender for 20 minutes at 32 rpm. The composition of the capsule fill material is given in the following table.

| Component | Material Class | Amount (wt %) |
|---|---|---|
| Intra-granular | | |
| SDD | dispersion of active and polymer | 66.67 |
| Extra-granular | | |
| Mannitol | Osmogen | 31.33 |
| Neusilin ® | Glidant | 2.00 |
| TOTAL | | 100.00 |

The formulation was then filled into 00 size HPMC (Vcaps® Plus) capsules, without tamping. Each capsule contained 300 mg of the formulation. The capsule of Example 6 was dissolution tested as described in Example 1. The results are included in FIG. 3.

Example 7

Granulated SDD Blended with Extragranular Sucrose Osmogen and Neusilin® Glidant

The SDD of Example 1 was used in this example. The SDD was granulated by slugging it and compressing to a solid fraction of 0.66. The slugs were then milled using a mortar and pestle, and passed through a 30 mesh screen. The granules were then mixed with the extra-granular materials in a Turbula blender for 20 minutes at 32 rpm. The composition of the capsule fill material is given in the following table.

| Component | Material Class | Amount (wt %) |
|---|---|---|
| Intra-granular | | |
| SDD | dispersion of active and polymer | 66.67 |
| Extra-granular | | |
| Sucrose | Osmogen | 31.33 |
| Neusilin ® | Glidant | 2.00 |
| TOTAL | | 100.00 |

The formulation was then filled into size 00 HPMC (Vcaps® Plus) capsules, without tamping. Each capsule contained 300 mg of the formulation. The capsule of Example 7 was dissolution tested as described in Example 1. The results are included in FIG. 3.

Control 1

SDD Granules Only

The SDD of example 1 was used as a control. The SDD was granulated by slugging the SDD and compressing to a solid fraction of 0.66. The slugs were then milled using a mortar and pestle, and passed through a 30 mesh screen. The granules were then mixed with the extra-granular (Neuslin) in a Turbula blender for 20 minutes at 32 rpm. The composition of the capsule fill material is given in the following table.

| Component | Material Class | Amount (wt %) |
|---|---|---|
| Intra-granular | | |
| SDD | dispersion of active and polymer | 98.00 |
| Extra-granular | | |
| Neuslin | Glidant | 2.00 |
| TOTAL | | 100.00 |

The formulation was then filled into size 00 HPMC (Vcaps® Plus) capsules, without tamping. Each capsule contained 204 mg of the formulation. The Control 1 was dissolution tested as described in Example 1. The results are included in FIG. 1, 2, 3.

Control 2

SDD Powder Alone Directly Filled into Capsule

The SDD of example 1 was used. The SDD was filled directly into size 00 HPMC (Vcaps® Plus) capsules, without tamping. Each capsule contained 200 mg of SDD. The capsule of Control 2 was dissolution tested as described in Example 1. The results are shown in FIG. 1.

Control 3

SDD Powder Blended with NaCl

The SDD of example 1 was used as a control. The SDD powder was blended with NaCl in a Turbula blender for 20 minutes at 32 rpm. The composition of the capsule fill material is given in the following table.

| Component | Material Class | Amount (wt %) |
|---|---|---|
| SDD | dispersion of active and polymer | 67.67 |
| NaCl | Osmogen | 33.33 |
| TOTAL | | 100.00 |

The formulation was then filled into size 00 HPMC (Vcaps® Plus) capsules, with light tamping. Each capsule contained 300 mg of the formulation. The capsule of Control 3 was dissolution tested as described in Example 1. The results are shown in FIG. 1.

Control 4

Granulated SDD and NaCl Osmogen

The SDD of example 1 was used as a control. The SDD was granulated by slugging the SDD and compressing to a solid fraction of 0.66. The slugs were then milled using a mortar and pestle, and passed through a 30 mesh screen. The granules were then mixed with the extra-granular NaCl in a Turbula blender for 20 minutes at 32 rpm. The composition of the capsule fill material is given in the following table.

| Component | Material Class | Amount (wt %) |
|---|---|---|
| | Intra-granular | |
| SDD | dispersion of active and polymer | 66.67 |
| | Extra-granular | |
| NaCl | Osmogen | 33.33 |
| TOTAL | | 100.00 |

The formulation was then filled into 00 HPMC (Vcaps® Plus) capsules, without tamping. Each capsule contained 300 mg of the formulation. The capsule of Control 4 was dissolution tested as described in Example 1. The results are shown in FIG. 1.

Control 5

Granulated SDD Blended with Extragranular Lactose Osmogen and Neusilin® Glidant

The SDD of Example 1 was used in this example. The SDD was granulated by slugging it and compressing to a solid fraction of 0.66. The slugs were then milled using a mortar and pestle, and passed through a 30 mesh screen. The granules were then mixed with the extra-granular materials in a Turbula blender for 20 minutes at 32 rpm. The composition of the capsule fill material is given in the following table.

| Component | Material Class | Amount (wt %) |
|---|---|---|
| | Intra-granular | |
| SDD | dispersion of active and polymer | 66.67 |
| | Extra-granular | |
| Lactose | Osmogen | 31.33 |
| Neusilin ® | Glidant | 2.00 |
| TOTAL | | 100.00 |

The formulation was then filled into size 00 HPMC (Vcaps® Plus) capsules, without tamping. Each capsule contained 300 mg of the formulation. The capsule of Control 5 was dissolution tested as described in Example 1. The results are shown in FIG. 1.

Control 6

The SDD of Example 1 was used as a control. The unencapsulated SDD powder was pre-wet by suspending in 50 mL of simulated gastric fluid. This 50 mL was added to an additional 200 mL of simulated gastric fluid, and a dissolution test was performed as described in Example 1. The results are shown in FIG. 1.

Contact Angle Measurements

Figure 4:
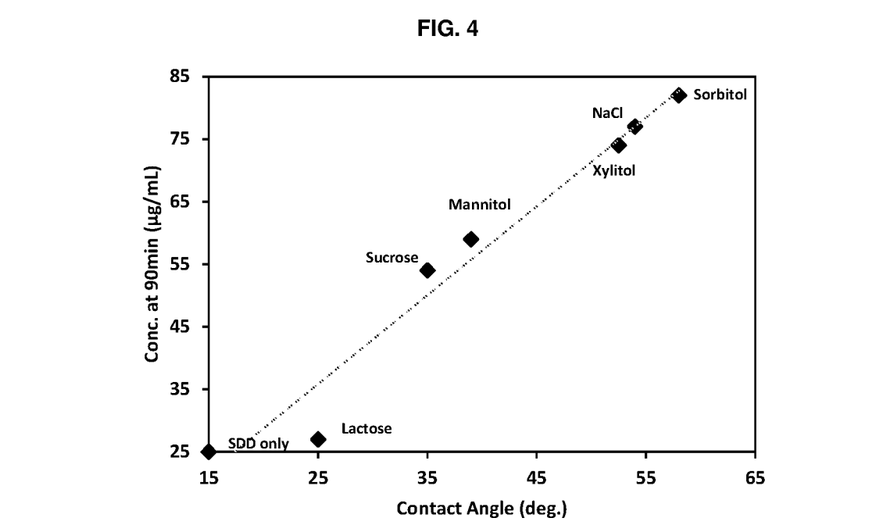
FIG. 4 shows the effect of contact angle with the concentration of active agent released after 90 minutes in a dissolution test.

Samples of the granulations with osmogen and glidant (i.e. granules from examples 1, 2B, 4, 6, 7, and controls 1 and 5) were formed into an 8-mm compact, and 1 drop of 0.01 HCl was added to the surface of the compact and a photograph was taken within 30 seconds to determine the contact angle with the formulations. The results of these measurements are given in FIG. 4.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A dosage form comprising a dissolvable capsule and a fill material, said fill material comprising
   a) a dispersion of an active agent and a polymer, said dispersion being granulated,
   b) an osmogen, wherein the osmogen is magnesium chloride, magnesium sulfate, lithium chloride, sodium chloride, potassium chloride, potassium hydrogen phosphate, lithium dihydrogen phosphate, sodium dihydrogen phosphate, potassium dihydrogen phosphate, potassium sulfate, sodium carbonate, sodium sulfite, lithium sulfate, sodium sulfate, magnesium succinate, glucose, sucrose, maltose, xylitol, sorbitol, glycerol, urea, inositol, tartaric acid, lactitol, maltitol, erythritol, or combinations thereof, and
   c) a glidant, wherein said glidant is silica, fumed silica, silicon dioxide, magnesium aluminosilicates, magnesium aluminometasilicates, or a mixture thereof, and comprises 0.5 wt % to 5 wt % of said fill material;
   wherein said dispersion comprises 10 wt % to 90 wt % of said fill material, said osmogen comprises from 15 wt % to 40 wt % of said fill material, and wherein the osmogen has a water solubility of at least 2.5 mol/kg, and a molecular weight of less than 500 Da.

2. The composition of claim 1 wherein the osmogen has a water solubility of at least 4 mol/kg, and a molecular weight of less than 500 Da.

3. The composition of claim 1 wherein the osmogen consists of sorbitol, NaCl, KCl, xylitol, or any combination thereof.

4. The composition of claim 1 wherein the polymer is selected from the group consisting of hydroxypropyl methyl cellulose acetate succinate (HPMCAS), hydroxypropyl methyl cellulose (HPMC), vinyl acetate/vinylpyrrolidone copolymers (PVPVA), polylactic acid, polyvinylpyrrolidone (PVP), poly(methacrylic acid-co-methyl methacrylate), poly(methacrylic acid-co-ethyl acrylate), and cellulose acetate phthalate (CAP).

5. The composition of claim 1 wherein the polymer is HPMCAS, HPMC, or PVPVA.

6. The composition of claim 1 wherein the polymer is HPMCAS or HPMC.

7. The composition of claim 1, wherein said dispersion is co-granulated with said osmogen such that the co-granulation consists of the dispersion and the osmogen.

8. The composition of claim 1, wherein said dispersion is co-granulated with said glidant such that the co-granulation consists of the dispersion and the glidant.

9. The composition of claim 1, wherein said capsule is an HPMC capsule.

10. A dosage form comprising a dissolvable capsule and a fill material, said fill material comprising
    a) a dispersion of an active agent and a polymer, said dispersion being granulated,
    b) an osmogen wherein the osmogen is magnesium chloride, magnesium sulfate, lithium chloride, sodium chloride, potassium chloride, potassium hydrogen phosphate, lithium dihydrogen phosphate, sodium dihydrogen phosphate, potassium dihydrogen phosphate, potassium sulfate, sodium carbonate, sodium sulfite, lithium sulfate, sodium sulfate, magnesium succinate, glucose, sucrose, maltose, xylitol, sorbitol, glycerol, urea, inositol, tartaric acid, lactitol, maltitol, erythritol, or combinations thereof, and
    c) a glidant;
wherein said dispersion comprises 10 wt % to 90 wt % of said fill material, said osmogen comprises from 15 wt % to 70 wt % of said fill material, and said glidant comprises at least 0.1 wt % of said fill material; and wherein the osmogen has a water solubility of at least 2.5 mol/kg, and a molecular weight of less than 500 Da.

11. The dosage form of claim 10 wherein said osmogen comprises from greater than 40 wt % to 70 wt % of said fill material.

12. The composition of claim 1, wherein the dispersion is co-granulated with the glidant and the osmogen such that the dispersion, glidant and osmogen are all co-granulated.

* * * * *